United States Patent
Hsu et al.

(10) Patent No.: US 9,980,935 B2
(45) Date of Patent: May 29, 2018

(54) METHOD OF TREATING HYPERGLYCEMIA

(71) Applicant: Center Laboratories, Inc., Taipei (TW)

(72) Inventors: Jui-Pao Hsu, Taipei (TW); Guang-Tzuu Shane, Taipei (TW); Meng-Ju Lee, Taipei (TW); Yi-Ping Liao, Taipei (TW); Yu-Yin Yeh, Taipei (TW)

( * ) Notice: Subject to any disclaimer, the term of this patent is extended or adjusted under 35 U.S.C. 154(b) by 0 days. days.

(21) Appl. No.: 15/597,200

(22) Filed: May 17, 2017

(65) Prior Publication Data

US 2017/0333382 A1 Nov. 23, 2017

Related U.S. Application Data

(60) Provisional application No. 62/339,131, filed on May 20, 2016.

(51) Int. Cl.
*A61K 31/277* (2006.01)
*A61K 31/155* (2006.01)
*A61K 45/06* (2006.01)

(52) U.S. Cl.
CPC .......... *A61K 31/277* (2013.01); *A61K 31/155* (2013.01); *A61K 45/06* (2013.01)

(58) Field of Classification Search
None
See application file for complete search history.

(56) References Cited

PUBLICATIONS

Sharma et al., Managing hypertension in diabetic patients—focus on trandolapril/verapamil combination, 2007, Vascular Health and Risk Management, 3(4), pp. 453-465.*
NIH, 2014, https://www.ncbi.nlm.nih.gov/pubmedhealth/PMH0072690/, pp. 1-3.*
Pfizer Reference ID: 3038080, Oct. 2011.*
Cho et al., Verapamil decreases the glucose-lowering effect of metformin in healthy volunteers, 2014, British Journal of Clinical Pharmacology, 78:6, pp. 1426-1432 (Year: 2014).*

* cited by examiner

*Primary Examiner* — Kortney L. Klinkel
*Assistant Examiner* — Tori Strong

(57) ABSTRACT

Disclosed herein are methods for treating conditions and/or disorders related to hyperglycemia. Such conditions and/or disorders related to hyperglycemia include, but are not limited to, type I, II diabetes mellitus, gestational diabetes, other forms diabetes, and disorders related thereto. In particular, the present invention relates to methods of using (R)-(+)-verapamil or a pharmaceutically acceptable salt thereof in the treatment of conditions and/or disorders related to hyperglycemia.

6 Claims, 4 Drawing Sheets

METHOD OF TREATING HYPERGLYCEMIA

CROSS-REFERENCES TO RELATED APPLICATIONS

This application claims the benefit of U.S. Provisional Application Ser. No. 62/339,131 filed May 20, 2016; the entire content of which is incorporated herein by reference.

BACKGROUND OF THE INVENTION

1. Field of the Invention

The present disclosure is generally directed to methods of treating to hyperglycemia, such as diabetes mellitus, with (R)-(+)-verapamil or a pharmaceutically acceptable salt thereof.

2. Description of Related Art

Diabetes mellitus is a condition in which a person's body does not produce enough, or does not properly respond to, insulin. Insulin is a hormone produced in the pancreas that enables cells to absorb glucose to turn it into energy. When insulin production is insufficient or when the body does not properly respond to insulin, glucose accumulates in the blood, which can lead to various complications. While there are several forms of diabetes, three forms are the most recognized: type I diabetes, type H diabetes, and gestational diabetes. Additionally, prediabetes is recognized as preceding diabetes and exists when blood glucose levels that are higher than normal but not yet high enough to be diagnosed as diabetes.

Type I diabetes or insulin-dependent diabetes mellitus (IDDM) is a metabolic disorder caused by destruction of the insulin-producing beta cells in the pancreas, which leads to insulin deficiency and high levels of glucose in plasma. The onset of type I diabetes generally results from an autoimmune etiology; however, idiopathic causes of beta cell destruction can occur for type I. Type 1 diabetes can affect children or adults, but was traditionally termed "juvenile diabetes" because it represents a majority of the diabetes cases in children.

Type II diabetes or non-insulin-dependent diabetes mellitus (NIDDM) has been found to possess inheritable aspects which can be greatly impacted by external environmental factors. The underlying etiologies of type II diabetes include deficiencies in insulin-producing beta cells; altered response to insulin by muscle, adipose, and liver cells; and abnormalities in the regulating mechanisms responsible for controlling carbohydrate and lipid metabolism following ingestion of food. Modulation in insulin-sensitivity is affected by environmental factors and behaviors, mostly a sedentary lifestyle and obesity. The cellular mechanisms that contribute to modulation of muscle and adipose cell sensitivity to insulin are complex and are not well understood. It is believed that altering insulin signaling pathways, increasing the amount of intracellular fat, and elevating levels of free fatty acids and other adipose tissue products can impact insulin-sensitivity.

Gestational diabetes occurs in pregnant women who have not previously been diagnosed with diabetes but who have high glucose levels during pregnancy. Gestational diabetes affects about 4% of all pregnant women and may precede development of type II diabetes.

If not properly controlled or stabilized, a hyperglycemic state has been associated with comorbidities including cardiovascular disease, vision impairment, various forms of neuropathy and cognitive impairment, stroke, and peripheral vascular disease. The common therapeutic approach, in addition to major modifications in an individual's dietary nutrition and physical activity, includes the use of anti-hyperglycemic drugs and insulin. Since the disease is chronic and progressive, and so far no treatment is able to reverse the progression, and thus there remains in this field a need of an improved medicament for treating conditions, diseases and/or disorders associated with hyperglycemia.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

The present invention relates to a medicament, which alone or in combination with any blood glucose reduction agent, do effectively reduce the blood glucose level of a hyperglycemia subject. The present invention therefore is useful for treating conditions related to hyperglycemia, which includes, but is not limited to, type I, type II diabetes mellitus, gestational diabetes, other forms of diabetes and/or disorders related thereto.

Accordingly, one aspect of the present disclosure relates to a novel use of (R)-(+)-verapamil or a pharmaceutically acceptable salt thereof, which is useful for the manufacture of a medicament for the treatment of conditions related to type I, type II diabetes mellitus, gestational diabetes, other forms of diabetes and/or disorders related thereto.

According to preferred embodiments of the present disclosure, the (R)-(+)-verapamil or a pharmaceutically acceptable salt thereof comprised in the medicament is in the form of a crystalline.

According to preferred embodiments of the present disclosure, the (R)-(+)-verapamil comprised in the medicament is in the form of hydrochloride salt.

According to embodiments of the present disclosure, the medicament further includes a blood glucose reduction agent, which may be selected from the group consisting of, glucagon-like peptide 1 (GLP-1) receptor agonist, dipeptidyl peptidase-4 (DPP-4) inhibitor, insulin, an insulin analogue, biguanide, sulfonylurea, thiazolidinedione (TZD), sodium-glucose co-transporter 2 (SGLT2) inhibitor, and α-glycosidase inhibitor.

According to embodiments of the present disclosure, the GLP-1 receptor agonist is liraglutide, exenatide, albiglutide or LY2189265.

According to embodiments of the present disclosure, the DPP-4 inhibitor is gliptins, sitagliptin, vildagliptin, saxagliptin, linagliptin, gemigliptin, anagliptin, teneligliptin, alogliptin, trelagliptin, dutogliptin, omarigliptin, berberine, and lupeol.

According to embodiments of the present disclosure, the insulin analogue is glargine, degludec or detemir.

According to embodiments of the present disclosure, the biguanide is metformin, phenformin, or bufomin. According to preferred embodiments of the present disclosure, the medicament comprises (R)-(+)-verapamil or a pharmaceutically acceptable salt thereof, and metformin.

According to embodiments of the present disclosure, the sulfonylurea is glibenclamide, gliclazide, glimepiride, or glipizide.

According to embodiments of the present disclosure, the TZD is pioglitazone, rosiglitazone, lobeglitazone, ciglitazone, darglitazone, englitazone, netoglitazone, rivoglitazone, or troglitazone.

According to embodiments of the present disclosure, the SGLT2 inhibitor is dapagliflozin, empagliflozin, canagliflozin, Ipragliflozin, tofogliflozin, sergliflozin etabonate, remogliflozin etabonat, or ertugliflozin.

According to embodiments of the present disclosure, the α-glycosidase inhibitor is acarbose, miglitose, or voglibose.

According to preferred embodiments of the present disclosure, the medicament comprising (R)-(+)-verapamil or a pharmaceutically acceptable salt thereof is suitable for oral, intravenous, intramuscular, intraperitoneal, intracranial, subcutaneous, transmucosal, or intrarectal administration. In one preferred embodiment, the medicament is administered orally. The medicament suitable for oral administration may be provided as tablets, pills, granules, powders, solutions, suspensions, syrups or capsules.

According to embodiments of the present disclosure, the medicament is administered in the amount from about 15 to 1,000 mg/day. Preferably, the medicament is administered in the amount from about 25 to 800 mg/day. More preferably, the medicament is administered in the amount from about 30 to 600 mg/day.

Another aspect of the present invention relates to a method of treating hyperglycemia, such as type I, type II diabetes mellitus, gestational diabetes, other forms of diabetes and/or disorders related thereto. The method includes administering to a subject suffering from diabetes mellitus and/or disorders related thereto, an effective amount of (R)-(+)-verapamil or a pharmaceutically acceptable salt thereof to alleviate or ameliorate the symptoms associated with diabetes mellitus.

According to preferred embodiments of the present disclosure, the (R)-(+)-verapamil or a pharmaceutically acceptable salt thereof is administered in the form of a crystalline.

According to preferred embodiments of the present disclosure, the (R)-(+)-verapamil is administered in the form of a hydrochloride salt.

According to embodiments of the present disclosure, the (R)-(+)-verapamil or a pharmaceutically acceptable salt thereof is administered in the amount from about 15 to 1,000 mg/day. Preferably, the (R)-(+)-verapamil or a pharmaceutically acceptable salt thereof is administered in the amount from about 25 to 800 mg/day. More preferably, the (R)-(+)-verapamil or a pharmaceutically acceptable salt thereof is administered in the amount from about 30 to 600 mg/day.

According to embodiments of the present disclosure, the (R)-(+)-verapamil or a pharmaceutically acceptable salt thereof is administered orally, intravenously, intramuscularly, intraperitoneally, intracranially, subcutaneously, transmucosally, or intrarectally. In one preferred embodiment, the (R)-(+)-verapamil or a pharmaceutically acceptable salt thereof is administered orally. The medicament suitable for oral administration may be provided as tablets, pills, granules, powders, solutions, suspensions, syrups or capsules.

According to embodiments of the present disclosure, the method further includes administering to the subject a blood glucose reduction agent, which may be selected from the group consisting of, glucagon-like peptide 1 (GLP-1) receptor agonist, dipeptidyl peptidase-4 (DPP-4) inhibitor, insulin, an insulin analogue, biguanide, sulfonylurea, thiazolidinedione (TZD), SGLT2 inhibitor, and α-glycosidase inhibitor.

According to embodiments of the present disclosure, the GLP-1 receptor agonist is liraglutide, exenatide, albiglutide or LY2189265.

According to embodiments of the present disclosure, the DPP-4 inhibitor is gliptins, sitagliptins, vildagliptin, saxagliptin, linagliptin, gemigliptin, anagliptin, teneligliptin, alogliptin, trelagliptin, dutogliptin, omarigliptin, berberine, and Lupeol.

According to embodiments of the present disclosure, the insulin analogue is glargine, degludec or detemir.

According to embodiments of the present disclosure, the biguanide is metformin, phenformin, or bufomin. According to preferred embodiments of the present disclosure, (R)-(+)-verapamil or a pharmaceutically acceptable salt thereof is administered along with metformin.

According to embodiments of the present disclosure, the sulfonylurea is glibenclamide, gliclazide, glimepiride, or glipizide.

According to embodiments of the present disclosure, the TZD is pioglitazone, rosiglitazone, lobeglitazone, ciglitazone, darglitazone, englitazone, netoglitazone, rivoglitazone, or troglitazone.

According to embodiments of the present disclosure, the SGLT2 inhibitor is dapagliflozin, empagliflozin, canagliflozin, Ipragliflozin, tofogliflozin, sergliflozin etabonate, remogliflozin etabonat, or ertugliflozin. According to embodiments of the present disclosure, the α-glycosidase inhibitor is acarbose, miglitose, or voglibose.

Many of the attendant features and advantages of the present disclosure will becomes better understood with reference to the following detailed description considered in connection with the accompanying drawings.

BRIEF DESCRIPTION OF THE DRAWINGS

The present description will be better understood from the following detailed description read in light of the accompanying drawings, where.

DESCRIPTION OF THE INVENTION

Figure 1:
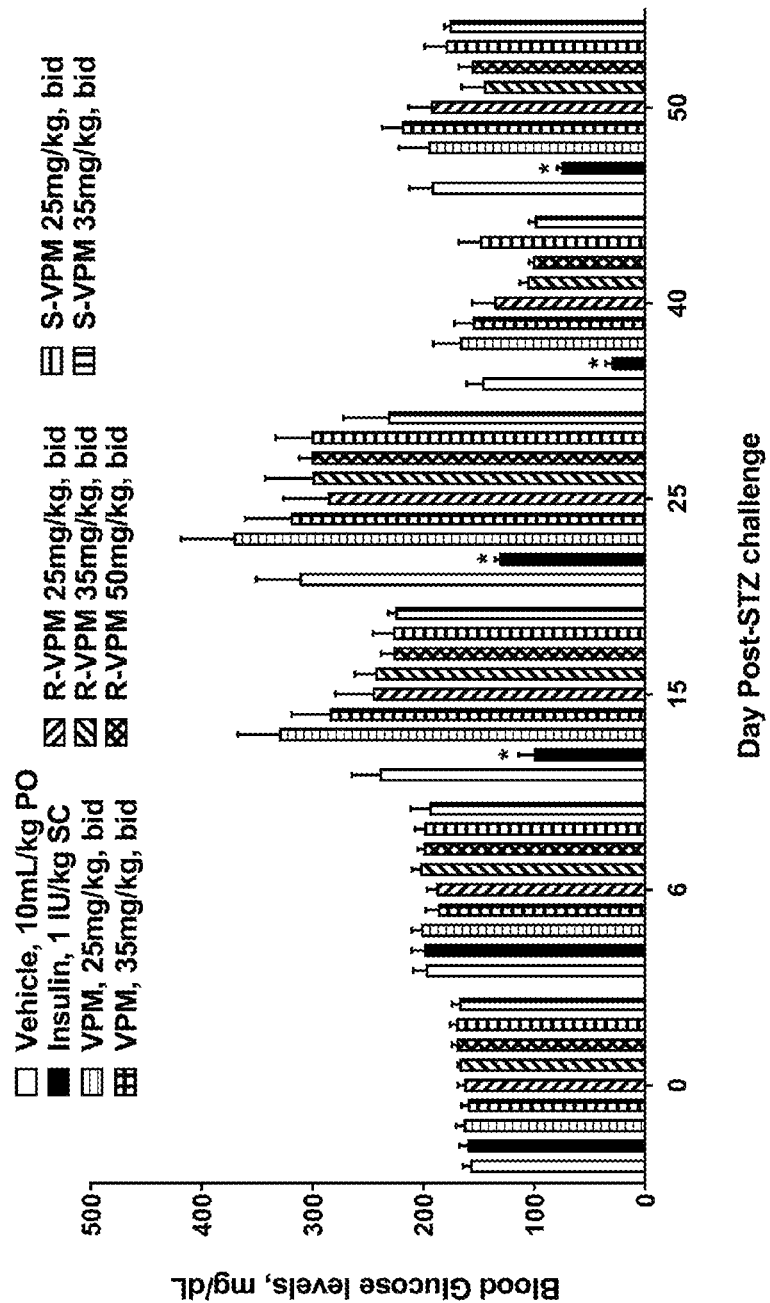
FIG. 1 is a bar graph illustrating the effects of racemic verapamil HCl, (R)-(+)-verapamil HCl and (S)-(−)-verapamil HCl on the level of blood glucose in STZ-induced diabetic mice in accordance with Example 1.1 of this invention.

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

1. Definitions

For convenience, certain terms employed in the specification, examples and appended claims are collected here. Unless defined otherwise, all technical and scientific terms used herein have the same meaning as commonly understood by one of the ordinary skill in the art to which this invention belongs.

The singular forms "a", "and", and "the" are used herein to include plural referents unless the context clearly dictates otherwise. The term "about" as used herein generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, or reflection angles disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

The term "diabetes mellitus" refers to type I, type II diabetes mellitus, gestational diabetes, and other forms of diabetes. Other forms diabetes may be latent autoimmune diabetes of adult (LADA), congenital diabetes, steroid diabetes, pancreatic defects related diabetes (e.g., chronic pancreatitis related diabetes, cystic fibrosis related diabetes, pancreatic neoplasia related diabetes, hemochromatosis related diabetes, and fibrocalculous pancreatopaty related diabetes), edocrinopathy related diabetes (e.g., acromegaly related diabetes, Crushing syndrome related diabetes, hyperthyroidism related diabetes, pheochromocytoma related diabetes, and glucagonoma related diabetes), infection related diabetes (e.g., cytomegalovirus infection related diabetes, and coxackievirus B related diabetes), diabetic angiopathy (e.g., diabetic retinopathy and diabetic nephropathy), and drug related diabetes (e.g., glucocorticoids related diabetes, thyroid hormone related diabetes, β-adrenergic agonists related diabetes, and statins related diabetes). Frequently correlated with type II diabetes mellitus are one or more of the metabolic syndrome, obesity, insulin resistance, dyslipidemia and a pathological glucose tolerance. Subjects with diabetes mellitus manifest varying degrees of increased blood pressure, increased levels of cholesterol and/or triglycerides, increased levels of uric acid and increased levels of factors that promote coagulation. Therefore, "disorders related to diabetes mellitus" as used herein refers to hypertension, hyperlipidemia, hyperuricemia, gout and hypercoagulability, i.e. an abnormal, increased tendency to form clots inside blood vessels. These disorders are well-recognized risk factors for atherosclerotic macrovascular as well as microvascular diseases. Atherosclerotic macrovascular diseases include myocardial infarction, stroke and limb amputation. Microvascular complications involve blindness, renal diseases and debilitating neuropathies.

The term "treatment" as used herein are intended to mean obtaining a desired pharmacological and/or physiologic effect, e.g., reducing blood glucose level in a hyperglycemia subject. The effect may be prophylactic in terms of completely or partially preventing a disease or symptom thereof and/or therapeutic in terms of a partial or complete cure for a disease and/or adverse effect attributable to the disease. "Treatment" as used herein includes, but is not limited to, preventative (e.g., prophylactic), curative or palliative treatment of a disease in a mammal, particularly human; and includes: (1) preventative (e.g., prophylactic), curative or palliative treatment of a disease or condition (e.g., diabetes mellitus or disorders related thereto) from occurring in an individual who may be pre-disposed to the disease but has not yet been diagnosed as having it; (2) inhibiting a disease (e.g., by promoting the proliferation of insulin-producing beta cells or suppressing apoptosis of these cells); or (3) relieving a disease (e.g., reducing symptoms associated with the disease).

The term "administered", "administering" or "administration" are used interchangeably herein to refer a mode of delivery, including, without limitation, orally, intravenously, intramuscularly, intraperitoneally, intraarterially, intracranially, transmucosally (e.g., inhalation, and intranasally), or subcutaneously administering of an agent (e.g., a compound or a composition) of the present invention. In preferred embodiments, the compound of the present disclosure (i.e., (R)-(+)-verapamil) is formulated into compositions that are suitable for oral administration.

The term "an effective amount" as used herein refers to an amount effective, at dosages, and for periods of time necessary, to achieve the desired result with respect to the treatment of a disease resulted from hyperglycemia. For example, in the treatment of diabetes mellitus, an agent (i.e., the present compound) which decrease, prevents, delays or suppresses or arrests any symptoms related to diabetes mellitus would be effective. An effective amount of an agent is not required to cure a disease or condition but will provide a treatment for a disease or condition such that the onset of the disease or condition is delayed, hindered or prevented, or the disease or condition symptoms are ameliorated. The specific effective or sufficient amount will vary with such factors as the particular condition being treated, the physical condition of the patient (e.g., the patient's body mass, age, or gender), the type of mammal or animal being treated, the duration of the treatment, the nature of concurrent therapy (if any), and the specific formulations employed and the like. Effective amount may be expressed, for example, as the total mass of the active agent (e.g., in grams, milligrams or micrograms) per day. The effective amount may be divided into one, two or more doses in a suitable form to be administered at one, two or more times throughout a designated time period.

The term "subject" or "patient" is used interchangeably herein and is intended to mean a mammal including the human species that is treatable by the compound of the present invention. The term "mammal" refers to all members of the class Mammalia, including humans, primates, domestic and farm animals, such as rabbit, pig, sheep, and cattle; as well as zoo, sports or pet animals; and rodents, such as mouse and rat. Further, the term "subject" or "patient" intended to refer to both the male and female gender unless one gender is specifically indicated. Accordingly, the term "subject" or "patient" comprises any mammal which may benefit from the treatment method of the present disclosure. Examples of a "subject" or "patient" include, but are not limited to, a human, rat, mouse, guinea pig, monkey, pig, goat, cow, horse, dog, cat, bird and fowl. In a preferred embodiment, the subject is a human.

The term "excipient" as used herein means any inert substance (such as a powder or liquid) that forms a vehicle/carrier for the active agent. The excipient is generally safe, non-toxic, and in a broad sense, may also include any known substance in the pharmaceutical industry useful for preparing pharmaceutical compositions such as, fillers, diluents, agglutinants, binders, lubricating agents, glidants, stabilizer, colorants, wetting agents, disintegrants, and etc.

The term "racemic" as used herein refers to a mixture of the (R)- and (S)-enantiomers, or stereoisomers, of verapamil in which neither enantiomer or stereoisomer is substantially purified from the other.

II. Treatment of Diabetes Mellitus and Disorders Related Thereto

Verapamil (e.g., 2-(3,4-dimethoxyphenyl)-5-[2-(3,4-dimethoxyphenyl)ethyl-methylamino]-2-propan-2-ylpentanenitrile) is a known drug with various medicinal indications. Traditionally, it is used for treating coronary disease, such as hypertension. The compound has a stereogenic center, hence can be separated into its optical enantiomers. The (S)-enantiomer is known to possess the majority of the calcium channel antagonist activity, whereas the (R)-enantiomer is known to possess agonist activity toward somatostatin receptor 2, and antagonist activity toward orexin receptors 1 and 2, dopamine $D_{2L}$ receptor, sodium and calcium channels (see WO 2011/057471A1); accordingly, the (R)-enantiomer is useful as a medicament for treating diseases or conditions related to these receptors in a human subject.

The present invention in general, relates to novel finding that (R)-(+)-verapamil, is more potent than racemic verapamil, or (S)-(−)-verapamil, in reducing the fasting blood glucose level in a diabetic subject. Accordingly, the (R)-(+)-verapamil, may be manufactured into a medicament for use in the treatment of diabetes mellitus and/or disorders related thereto.

In this regard, a particular aspect of the present invention relates to a method of treating a subject suffering from diabetes mellitus and/or disorders related thereto. The method includes the step of, administering to the subject an effective amount of (R)-(+)-verapamil or a pharmaceutically acceptable salt thereof (e.g., (R)-(+)-verapamil HCl), so as to ameliorate or alleviate symptoms associated to diabetes mellitus and/or disorders related thereto.

(R)-(+)-verapamil may be obtained from racemic mixture of verapamil by high performance liquid chromatography (HPLC) separation or resolution of the enantiomers using any available means, such as optically active resolving acid. Alternatively, (R)-(+)-verapamil may be synthesized by stereospecific synthesis using any method known in the related art. Stereospecific synthesis in general can result in products with high enantiomeric purity. In cases when the enantiomeric purity is not sufficient, then the synthetic product may be subject to further purification process to enhance the enantiomeric purity by separating (R)-(+)-verapamil from (S)-(−)-verapamil. Examples of processes for resolving racemic verapamil to produce (R)-(+)-verapamil are well known to those of ordinary skill in the art.

According to some preferred embodiments, the (R)-(+)-verapamil or a pharmaceutically acceptable salt thereof is administered in a crystalline form. The crystalline of (R)-(+)-verapamil or a pharmaceutically acceptable salt thereof may be produced by any known crystallization method, e.g., saturation method. In one example, (R)-(+)-verapamil HCl is dissolved in suitable solvent(s), which include but are not limited to, ethyl acetate, toluene, and 1,4-dioxane/heptane (1:1), until a saturated solution is obtained; the saturated solution is then cooled to form (R)-(+)-verapamil HCl crystals therefrom.

According to preferred embodiments, the (R)-(+)-verapamil suitable for use in the present invention is in the form of hydrochloride salt, that is, (R)-(+)-verapamil HCl.

According to optional embodiments, the (R)-(+)-verapamil or a pharmaceutically acceptable salt thereof may be administered with one or more active compounds other than (R)-(+)-verapamil to ameliorate or alleviate the hyperglycemia state of the subject. In some preferred embodiments, the one or more active compound is a blood glucose reduction agent. Any known blood glucose reduction agent may be used. Preferably, the blood glucose reduction agent is a glucagon-like peptide 1 (GLP-1) receptor agonist, a dipeptidyl peptidase-4 (DPP-4) inhibitor, insulin, an insulin analogue, biguanide, sulfonylurea, thiazolidinedione (TZD), sodium-glucose co-transporter 2 (SGLT2) inhibitor, or α-glycosidase inhibitor.

Suitable examples of the GLP-1 receptor agonist include, but are not limited to, liraglutide, exenatide, albiglutide or LY2189265.

DPP-4 inhibitor is gliptins, and suitable examples of gliptins include, but are not limited to, sitagliptin, vildagliptin, saxagliptin, linagliptin, gemigliptin, anagliptin, teneligliptin, alogliptin, trelagliptin, dutogliptin, omarigliptin, berberine, and lupeol.

The term "insulin" as used herein refers to purified, synthetic and/or biotechnologically derived products that are the same as, or similar to, naturally occurring insulins in structure, use, and intended effect and are of value in the treatment of diabetes mellitus. For example, insulin may be directly recovered from pancreatic tissues of a mammal, such as pancreas glands of farm animals (e.g., pig). Alternatively, insulin may be produced by recombinant technology.

Examples of the insulin analogue include, but are not limited to, glargine, degludec and detemir.

Suitable examples of the biguanide include, but are not limited to, metformin, phenformin, and bufomin.

Suitable examples of sulfonylurea include, but are not limited to, glibenclamide, gliclazide, glimepiride, and glipizide.

Examples of TZD include, but are not limited to, pioglitazone, rosiglitazone, lobeglitazone, ciglitazone, darglitazone, englitazone, netoglitazone, rivoglitazone, and troglitazone.

Examples of SGLT2 inhibitors include, but are not limited to, dapagliflozin, empagliflozin, canagliflozin, Ipragliflozin, tofogliflozin, sergliflozin etabonate, remogliflozin etabonat, and ertugliflozin.

Suitable examples of the α-glycosidase inhibitor include, but are not limited to, acarbose, miglitose, and voglibose.

According to embodiments of the present disclosure, (R)-(+)-verapamil or a pharmaceutically acceptable salt thereof may be administered to the subject in need of such treatment in the amount of 15 to 1,000 mg/day, such as 15, 20, 25, 30, 35, 40, 50, 60, 70, 75, 80, 90, 100, 110, 120, 125, 130, 140, 150, 160, 170, 175, 180, 190, 200, 210, 220, 230, 240, 250, 260, 270, 280, 290, 300, 310, 320, 330, 340, 350, 360, 370, 375, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1,000 mg/day; preferably, the (R)-(+)-verapamil or a pharmaceutically acceptable salt thereof is administered in the amount from about 25 to 800 mg/day, such as 25, 30, 35, 40, 50, 60, 70, 75, 80, 90, 100, 110, 120, 125, 130, 140, 150, 160, 170, 175, 180, 190, 200, 210, 220, 230, 240, 250, 260, 270, 280, 290, 300, 310, 320, 330, 340, 350, 360, 370, 375, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800 mg/day; more preferably, the (R)-(+)-verapamil or a pharmaceutically acceptable salt thereof is administered in the amount from about 30 to 600 mg/day, such as 30, 35, 40, 50, 60, 70, 75, 80, 90, 100, 110, 120, 125, 130, 140, 150, 160, 170, 175, 180, 190, 200, 210, 220, 230, 240, 250, 260, 270, 280, 290, 300, 310, 320, 330, 340, 350, 360, 370, 375, 380, 390, 400, 410, 420, 430, 440, 450, 460, 470, 480, 490, 500, 510, 520, 530, 540, 550, 560, 570, 580, 590, 600 mg/day.

According to preferred embodiments, (R)-(+)-verapamil or a pharmaceutically acceptable salt thereof is administered to a subject in need thereof along with metformin, in which the combined treatment results in synergistically reduction in the levels of blood glucose and glycated haemolglobin (HbA1c).

According to embodiments of the present disclosure, the (R)-(+)-verapamil or a pharmaceutically acceptable salt thereof may be administered via any suitable route, which includes, but is not limited to, oral, intraveneous, intramuscular, intraperitoneal, intraarterial, intracranial, and subcutaneous route. In preferred embodiment, an effective amount of (R)-(+)-verapamil hydrochloride is orally administered to the subject in need thereof.

In further embodiment, the method is for the treatment of diabetes that responses poorly to oral hyperglycemia agent.

A further aspect of the present invention relates to a pharmaceutical composition for the treatment of diabetes mellitus and/or disorders related thereto.

The composition comprises an effective amount of (R)-(+)-verapamil or a pharmaceutically acceptable salt thereof; and a pharmaceutically acceptable excipient.

To produce the pharmaceutical composition, (R)-(+)-verapamil or a pharmaceutically acceptable salt thereof, preferably, a crystalline of (R)-(+)-verapamil, is mixed with suitable excipients and formulated into a dosage form suitable for administering orally, intraveneously, intramuscularly, intraperitoneally, intraarterially, intracranially, transmucosally (e.g., inhalation, buccal, and intranasally), or subcutaneously. Suitable excipients are known to those of skill in the art and described, for example, in Handbook of Pharmaceutical Excipients (Kibbe (ed.), 3$^{rd}$ Edition (2000), American Pharmaceutical Association, Washington, D.C.), and Remington's Pharmaceutical Sciences (Gennaro (ed.), 20$^{th}$ edition (2000), Mack Publishing Inc., Easton, Pa.), which for their disclosure relating to excipients and dosage forms, are incorporated herein by reference. For example, suitable excipients include, but are not limited to, starches, sugars, microcrystalline cellulose, diluents, granulating agents, lubricants, binders, disintegrating agents, wetting agents, lubricants, emulsifiers, coloring agent, release agents, coating agents, sweetening agents, flavoring agents, preservatives, plasticizers, gelling agents, thickeners, hardeners, setting agents, suspending agents, surfactants, humectants, carriers, stabilizers, antioxidants, and combinations thereof.

The pharmaceutical composition are typically provided in dosage forms suitable for administration to a subject by any desired route. One of skill in the art is familiar with various dosage forms that are suitable for use in the present invention. The most suitable route in any given case will depend on the nature and severity of the disease being treated and/or managed. For example, the pharmaceutical compositions may be formulated for administration orally, intraveneously, intramuscularly, intraperitoneally, intraarterially, intracranially, transmucosally (e.g., inhalation, buccal, and intranasally), or subcutaneously. Preferably, the pharmaceutical composition is administered orally.

The dosage form of the pharmaceutical composition suitable for oral administration includes, for example, tablets, pills, granules, powders, solutions, suspensions, syrups or capsules. As a method of producing solid dosage form such as a tablet, a pill, granule or powder, it can be formed by conventional techniques using a pharmaceutically acceptable carrier such as excipient, binder, or disintegrant and etc. The solid dosage form for oral administration may optionally be scored or prepared with coating and shells, such as entering coatings, and coatings for modifying the rate of release. Further, any of the solid dosage form may be encapsulated in soft and hard gelatin capsules using any of the excipients known in the art.

(R)-(+)-verapamil or a pharmaceutically acceptable salt thereof may also be formulated into a liquid dosage form for oral administration. Suitable formulation include emulsion, solutions, suspension or syrup, it can be produced by conventional techniques using diluents commonly used in the art, such as water, glycerol esters, alcohols, vegetable oils, and etc. The liquid formulation may optionally include adjuvants such as wetting agents, emulsifying agents, and suspending agents, sweetening, flavoring, coloring, and preservative agents. The liquid formulation may also be filled into soft gelatin capsules. For example, the liquid may include a solution, suspension, emulsion, precipitate, or any other desired liquid media carrying the (R)-(+)-verapamil. The liquid may be designed to improve the solubility of the (R)-(+)-verapamil upon release, or may be designed to form a drug-containing emulsion or dispersed phase upon release. Examples of such techniques are well known in the related art. Soft gelatin capsules may be coated, as desired, with a functional coating, such as to delay the release of the drug.

In the case of parenteral administration, (R)-(+)-verapamil or a pharmaceutically acceptable salt thereof may be formulated into injectable forms for intravenous, subcutaneous or intramuscular administration. An injection can be prepared by dissolving the compound the present disclosure (e.g., (R)-(+)-verapamil, (R)-(+)-verapamil HCl, or a crystalline thereof) in water soluble solution such as physiological saline, or water insoluble solution consisting of organic esters such as propylene glycol, polyethylene glycol, or vegetable oils (e.g., sesame oil).

In the case of transdermal administration, for example, a dosage form as an ointment or a cream can be employed. The ointment can be produced by mixing the compound the present disclosure (e.g., (R)-(+)-verapamil, (R)-(+)-verapamil HCl, or a crystalline thereof) with fats or oils and etc; and the cream can be produced by mixing compound the present disclosure (e.g., (R)-(+)-verapamil, (R)-(+)-verapamil HCl, or a crystalline thereof) with emulsifiers. The transdermal formulation may be a liquid or a powdery formulation. In a liquid formulation water, salt solution, phosphate buffer, acetate buffer and etc may be used as a base; it may also contain surfactants, antioxidants, stabilizers, preservatives or tackifiers. In a powdery formulation, it may contain water-absorbing materials such as water-soluble polyacrylates, cellulose low-alkyl esters, polyethylene glycol polyvinyl pyrrolidone, amylase and etc, and non-water absorbing materials such as cellulose, starches, gums, vegetable oils or cross-linked polymers. Further, antioxidants, colorants, preservatives may be added to the powdery formulation. The liquid or powdery formulation may be administered by use of a spray apparatus.

In the case of rectal administration, it may be in the form of suppository using a gelatin soft capsule.

In case of inhalation through nose or mouth, a solution or suspension containing the compound the present disclosure (e.g., (R)-(+)-verapamil, (R)-(+)-verapamil HCl, or a crystalline thereof) and a pharmaceutical excipient generally accepted for this purpose is inhaled through an inhalant aerosol spray. Alternatively, the compound the present disclosure (e.g., (R)-(+)-verapamil, (R)-(+)-verapamil HCl, or a crystalline thereof) in the form of a powder may be administered through inhalator that allows direct contact of the powder with the lung. To these formulations, if necessary, pharmaceutical acceptable carriers such as isotonic agents, preservatives, dispersions, or stabilizers may be added. Further, if necessary, these formulations may be sterilized by filtration, or by treatment with heat or irradiation.

The effective amount of (R)-(+)-verapamil or a pharmaceutically acceptable salt thereof of the present disclosure suitable for treating diabetes mellitus and/or disorders related thereto varies with the route of administration, or condition, age, sex, or weight of the subject receiving the treatment. In general, (R)-(+)-verapamil or a pharmaceutically acceptable salt thereof is to administered to the subject in single or divided doses 2, 3, 4 or more times each day. Alternatively, the dose may be delivered once every 2, 3, 4, 5 or more days. In one preferred embodiment, the pharmaceutical composition is administered once per day. In another embodiment, the pharmaceutical composition is administered twice per day. The effective amount of (R)-(+)-verapamil or a pharmaceutically acceptable salt thereof to be administered is about 15-1,000 mg/day, such as 15, 20, 25, 30, 35, 40, 50, 60, 70, 75, 80, 90, 100, 110, 120, 125, 130, 140, 150, 160, 170, 175, 180, 190, 200, 210, 220, 230, 240, 250, 260, 270, 280, 290, 300, 310, 320, 330, 340, 350, 360, 370, 375, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1,000 mg/day; preferably, the (R)-(+)-verapamil or a pharmaceutically acceptable salt thereof is administered in the amount from about 25 to 800 mg/day, such as 25, 30, 35, 40, 50, 60, 70, 75, 80, 90, 100, 110, 120, 125, 130, 140, 150, 160, 170, 175, 180, 190, 200, 210, 220, 230, 240, 250, 260, 270, 280, 290, 300, 310, 320, 330, 340, 350, 360, 370, 375, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800 mg/day; more preferably, the (R)-(+)-verapamil or a pharmaceutically acceptable salt thereof is administered in the amount from about 30 to 600 mg/day, such as 30, 35, 40, 50, 60, 70, 75, 80, 90, 100, 110, 120, 125, 130, 140, 150, 160, 170, 175, 180, 190, 200, 210, 220, 230, 240, 250, 260, 270, 280, 290, 300, 310, 320, 330, 340, 350, 360, 370, 375, 380, 390, 400, 410, 420, 430, 440, 450, 460, 470, 480, 490, 500, 510, 520, 530, 540, 550, 560, 570, 580, 590, 600 mg/day.

Any of the pharmaceutical composition and dosage forms described above may further comprise one or more active compounds other than (R)-(+)-verapamil, to manage the same condition being treated by (R)-(+)-verapamil or a pharmaceutically acceptable salt thereof. In some embodiments, blood glucose reduction agents are included in the pharmaceutical compositions. Preferably, the blood glucose reduction agent is a glucagon-like peptide 1 (GLP-1) receptor agonist, a dipeptidyl peptidase-4 (DPP-4) inhibitor, insulin, an insulin analogue, biguanide, sulfonylurea, thiazolidinedione (TZD), SGL-T2 inhibitor, or α-glycosidase inhibitor.

Suitable examples of the GLP-1 receptor agonist include, but are not limited to, liraglutide, exenatide, albiglutide and LY2189265.

DPP-4 inhibitor is gliptins, and suitable examples of gliptins include, but are not limited to, sitagliptin, vildagliptin, saxagliptin, linagliptin, gemigliptin, anagliptin, teneligliptin, alogliptin, trelagliptin, dutogliptin, omarigliptin, berberine, and lupeol.

Insulin as used herein refers to purified, synthetic and/or biotechnologically derived products that are the same as, or similar to, naturally occurring insulins in structure, use, and intended effect and are of value in the treatment of diabetes mellitus. For example, insulin may be directly recovered from pancreatic tissues of a mammal, such as pancreas glands of farm animals (e.g., pig). Alternatively, insulin may be produced by recombinant technology.

Examples of the insulin analogue include, but are not limited to, glargine, degludec and detemir.

Preferred examples of the biguanide include, but are not limited to, metformin, phenformin, or bufomin.

Suitable examples of sulfonylurea include, but are not limited to, glibenclamide, gliclazide, glimepiride, and glipizide.

Examples of TZD include, but are not limited to, pioglitazone, rosiglitazone, lobeglitazone, ciglitazone, darglitazone, englitazone, netoglitazone, rivoglitazone, and troglitazone.

Examples of the SGLT2 inhibitor include, but are not limited to, dapagliflozin, empagliflozin, canagliflozin, Ipragliflozin, tofogliflozin, sergliflozin etabonate, remogliflozin etabonat, and ertugliflozin.

Suitable example of the α-glycosidase inhibitor include, but are not limited to, acarbose, miglitose, and voglibose.

In preferred embodiment, the pharmaceutical composition comprises an effective amount of (R)-(+)-verapamil or a pharmaceutically acceptable salt thereof and metformin.

In optional embodiments, the one or more active compounds other than (R)-(+)-verapamil or a pharmaceutically acceptable salt thereof (e.g., the blood glucose reduction agent) may be provided in a separate formulation and co-administered to the subject with the present pharmaceutical composition. Such separate formulations may be administered before, after, or simultaneously with the administration of the present composition comprising (R)-(+)-verapamil or a pharmaceutically acceptable salt thereof.

The present invention will now be described in further detail with reference to the following examples. However, it should be understood that the present invention is not limited to the specified examples.

EXAMPLES

Materials and Methods

Materials.

(R)-(+)-verapamil HCl, (S)-(−)-verapamil HCl as well as the racemic mixture were respectively provided by Center Laboratories Inc (Taipei, Taiwan, R.O.C.). Glucometer was purchased from Abbott (USA). Glucose assay kits were purchased form Denka Seiken Co. Ltd (Tokyo, Japan). Insulin and metformin were both from Sigma-Aldrich (USA), and HbA1c assay kits were from Fujirebio (Japan).

Animals.

Wide-type male C57BL/6 mice (each weighted about 20-25 g), non-insulin dependent diabetic mellitus (NIDDM) male db/db mice (C57BLKS/J lar-+$Lepr^{db}$/+$Lepr^{db}$, each weighted about 45±10 g) and db/m+ (C57BLKS/J Lar- m+/+$Lepr^{db}$) mice were used in the present study.

C57BL/6 mice were provided by BioLASCO Taiwan (authorized by Charles River Laboratory, Wilmington, Mass.).

NIDDM mice and db/m+ mice were provided by Institute for Animal Reproduction (IAR, Japan). They exhibited hyperinsulinemia, hyperglycemia, and islet atrophy and were used at about 10-12 weeks of age. These animals were housed singly in Individually Ventilated cages Racks (IVC Racks, 36 Mini Isolator systems (Tecniplast, Italy) throughout the study.

All were maintained in the animal facility with controlled temperature (20-24° C.), humidity (50-80%) and a 12 h/12 h light/dark cycle (light on at 7:00 a.m.) with food and water provided ad libitum. Experimental procedures for handling the mice complied with relevant regulations set forth in "Guide for the Care and Use of Laboratory Animals: Eighth Edition" (National Academies Press, Washington, D.C., 2011) in AAALAC-accredited laboratory animal facility. (Eurofins Panlabs Taiwan, Ltd.)

STZ-Induced Diabetic Mice and Treatment

Wide-type male C57BL/6 mice were rendered diabetic by multiple intraperitoneal injection of streptozotocin (STZ, 40 mg/Kg/day for 5 days, day 1 to day 5). Mice exhibited an averaged blood glucose level greater than 160 mg/dL on day 6 were selected for subsequent study. The vehicle or test compound (i.e., verapamil HCl in racemic form (VPM, bid), (R)-(+)-verapamil HCl (R-VPM, bid) or (S)-(-)-verapamil HCl (S-VPM, bid)) at the designated dose was orally fed to each mice twice daily from day 6, and continued for 44 days to day 49. For animals treated with insulin, insulin was administered subcutaneously 90 minutes before blood glucose measurement. Non-fasting blood glucose level was measured on days 6, 15, and 25, whereas fasting blood glucose (i.e., blood glucose level after fasting for 12 hrs fasting) was measured on days 40 and 50.

NIDDM Mice and Treatment

NIDDM mice and db/m+ mice (the sham control) were acclimated at least one week and then grouped for treatment when the average blood glucose value was ≥350 mg/dl after 6-hr fasting. Test compounds (i.e., verapamil HCl in racemic form (VPM, bid), (R)-(+)-verapamil HCl (R-VPM, bid), (S)-(-)-verapamil HCl (S-VPM, bid), metformin (once daily), or the combination of R-VPM (bid) and metformin (Met, once daily)) at the designated dose was orally fed to each mice from day 1, and continued for 44 consecutive days to day 45 (EXAMPLE 1.2) or for 42 consecutive days to day 43 (EXAMPLE 2). Blood glucose and glycated haemoglobin (HbA1c) levels were measured on designated days after 6-hr fasting. Body weight of each test animal was also measured during the study period.

It was noted that during the pre-run of this experiment (EXAMPLE 1.2), administration of 50 mg/Kg, bid of VPM or S-VPM resulted in death of all the test animals, thus, in this experiment, the dose of VPM or S-VPM was set to be not more than 50 mg/Kg, bid (such as 15 or 30 mg/Kg, bid). The dose for R-VPM, on the other hand, was not bound by such limitation.

Statistics

Results were expressed as the mean±standard error of the mean (SEM). Unpaired student's t-test or 1-way ANOVA followed by Dunnett's test was used for statistical comparisons between substance-treated and vehicle-treated groups. Differences are considered significant at †P<0.05, vs vehicle control (db/m+); *P<0.05, vs vehicle control (db/db or STZ-induced mice); #P<0.05, vs metformin (db/db). Comparisons of "Met" and "vehicle control (db/db)" by Student's unpaired t-test: significance denoted by solid lines and trends denoted by dashed lines.

Example 1 Effects of (R)-(+)-Verapamil HCl on Blood Glucose Level in Diabetic Mice 1.1 STZ-Induced Diabetic Mice In this example, the effects of racemic verapamil HCl (VPM), (R)-(+)-verapamil HCl (R-VPM) or (S)-(-)-verapamil HCl (S-VPM) was evaluated in STZ-induced diabetic animals in accordance with procedures described in the "Materials and Methods" section. Results are illustrated in FIG. 1.

As depicted in FIG. 1, insulin was capable of reducing the level of non-fasting or fasting blood glucose in STZ-induced diabetic animals, whereas racemic verapamil (25 or 35 mg/Kg, bid) had no effects on either fasting or non-fasting blood glucose level. As to the effects of (R)-(+)-verapamil HCl and (S)-(-)-verapamil HCl, it appeared that (R)-(+)-verapamil HCl was relatively more potent than (S)-(-)-verapamil HCl in reducing the level of fasting blood glucose.

1.2 Non-Insulin Dependent Diabetic Mellitus (NIDDM) Mice

Figure 2:
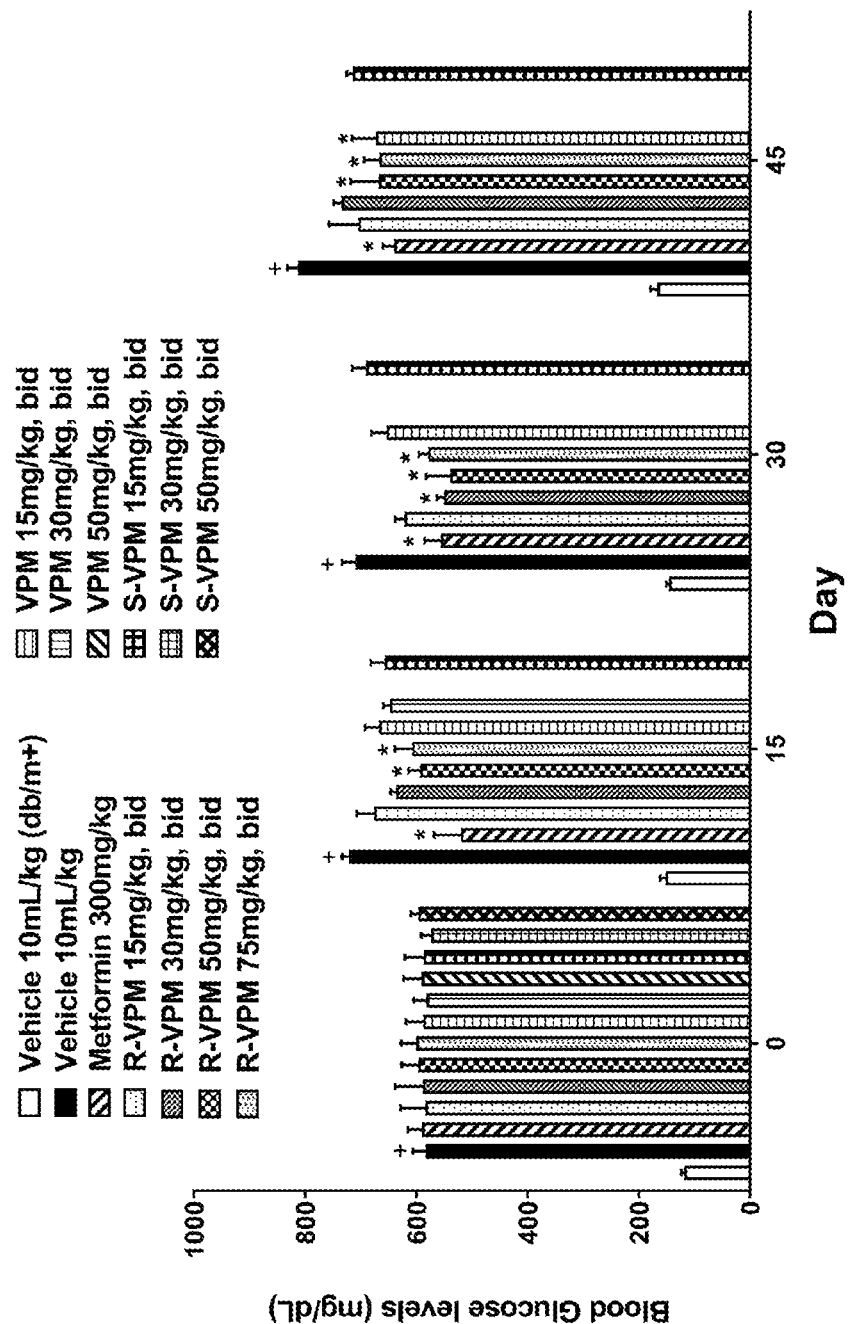
FIG. 2 is a bar graph illustrating the effects of racemic verapamil HCl, (R)-(+)-verapamil HCl and (S)-(−)-verapamil HCl on the level of blood glucose in NIDDM mice in accordance with Example 1.2 of this invention.

In this example, the effects of racemic verapamil HCl (VPM), (R)-(+)-verapamil HCl (R-VPM) or (S)-(-)-verapamil HCl (S-VPM) on blood glucose level were evaluated by use of NIDDM mice, which were born with mild defects in the insulin signaling cascade that gave rise to insulin resistance and subsequent progression to a diabetic phenotype. For comparison, a group of 5 db/m+ (C57BLKS/J Lar- m+/+$Lepr^{db}$) mice were used as the sham control. Blood glucose levels were measured on day 0 (before treatment), and on days 15, 30, and 45 in the 6-hr fasting animals. Results are illustrated in FIG. 2.

As expected, metformin (300 mg/Kg) reduced the level of fasting blood glucose in NIDDM mice; however, neither racemic verapamil HCl (30 mg/Kg, bid) nor (S)-(-)-verapamil HCl, possessed any effect on reduction of fasting blood glucose level. By contrast, (R)-(+)-verapamil HCl at the doses of 50 and 75 mg/Kg, bid respectively reduced the fasting blood glucose level, as compared with that of the control vehicle NIDDM mice.

Example 2 Combined Treatment of (R)-(+)-Verapamil HCl and Metformin Synergistically Reduced Blood Glucose Level and Glycated Haemolglobin (HbA1c) Level in NIDDM Mice Based on the finding of example 1.2, the combined effects of metformin and (R)-(+)-verapamil HCl (R-VPM) on fasting blood glucose and glycated hemolglobin (HbA1c) were further evaluated in NIDDM mice. For comparison, a group of 8 db/m+(C57BLKS/J Lar- m+/+$Lepr^{db}$) mice were used as the sham control. Levels of blood glucose and HbA1c were respectively measured on day 0 (before treatment), and on day 15, 29 and 43 in the 6-hr fasting animals. Results are provided in FIGS. 3 and 4; and Tables 1 to 6.

2.1 Blood Glucose Level

Figure 3:
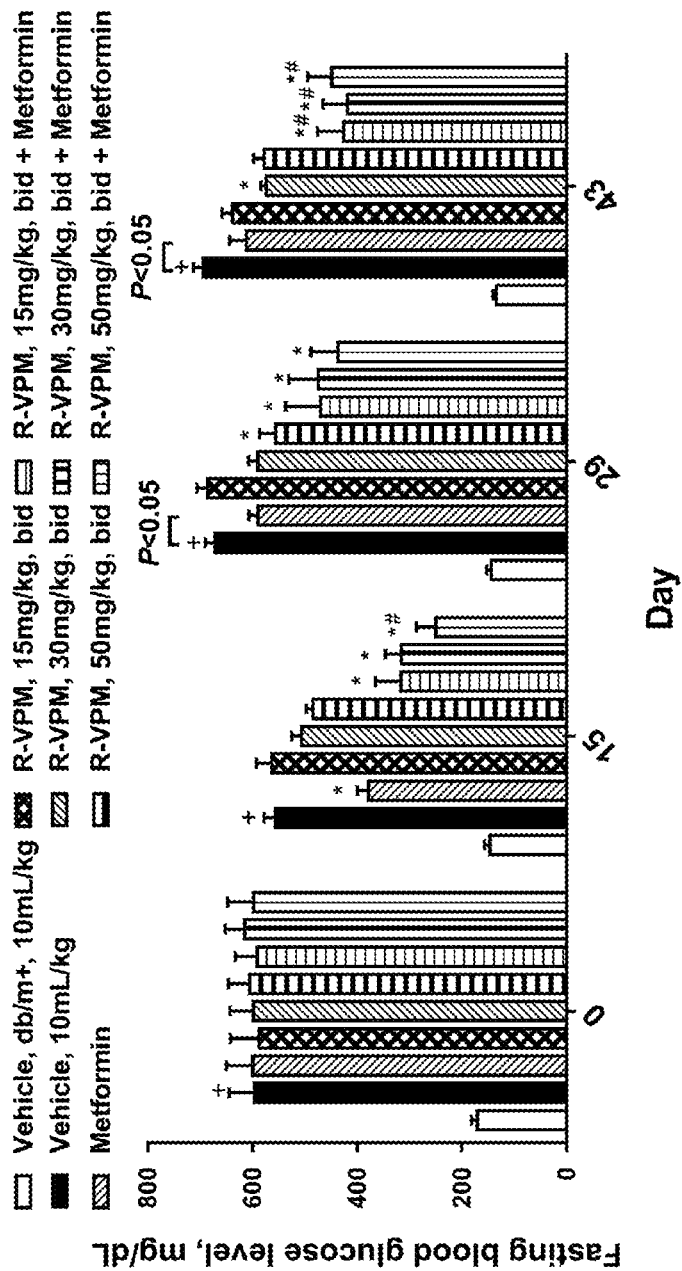
FIG. 3 is a bar graph illustrating the effects of (R)-(+)-verapamil HCl and/or metformin on the level of blood glucose in NIDDM mice in accordance with Example 2.1 of this invention, in which differences are considered significant at †$P<0.05$, vs vehicle control (db/m+), *$P<0.05$, vs vehicle control (db/db), #$P<0.05$, vs metformin (db/db). Comparisons of "metformin" and "vehicle control (db/db" is performed using Student's unpaired t-test: significance denoted by solid lines.

Referring to FIG. 3, as expected, metformin could reduce the blood glucose levels of NIDDM mice on days 15, 29 and 43, so did (R)-(+)-verapamil HCl (R-VPM) at higher dose (i.e., 30 or 50 mg/Kg, bid). More surprisingly, the combined treatment of R-VPM and metformin exhibited a synergistic effect on the reduction of blood glucose level, even in the case when low dose R-VPM (i.e., 15 mg/Kg, bid) was administered, which dose was ineffective in reducing blood glucose level on its own.

Referring to Table 1, which summarizes the relative blood glucose levels collected from NIDDM mice treated with (R)-(+)-verapamil HCl (R-VPM, 15 mg/kg, bid), metformin (300 mg/Kg) or both, as compared to the respective control levels in the present study. In Table 1, blood glucose level in each treatment group was expressed as % of the control, which was the blood glucose level on day 0 and was taken to be 100%. In the "vehicle" group, it was found that blood glucose levels were respectively 97.1%, 116.4% and 121.6% over that of the control on days 15, 29, and 43 (see column A in Table 1). In the "metformin" group, blood glucose levels on days 15, 29, and 43 were respectively 65.3%, 103.6% and 108.8% over that of day 0 (i.e., column B), when these values were compared with those in the "vehicle" group, it was apparent that metformin successfully reduced blood glucose level for about 31.8%, 12.8%, and 12.8% on days 15, 29 and 43 (i.e., column C). As to the effect of R-VPM, blood glucose levels were even higher than those of the control (column D vs column A), and no reduction in blood glucose level was observed (i.e., column E); indicating that (R)-(+)-verapamil HCl at the dose of 15 mg/kg, bid possessed no treatment effect. By contrast, the combined treatment of R-VPM and metformin resulted in about 42.5%, 35% and 47.6% reduction in blood glucose levels on days 15, 29, and 43 (column H), which were much lower than the summation of blood glucose changes resulted by metformin alone and R-VPM alone (column H vs column F). Taken together, the data suggested that the combined treatment of R-VPM and metformin may synergistically reduce blood glucose level in diabetic animals, in which the reduction were about 1.44, 4.61 and 2.45 folds (i.e., column I) over that of the control (i.e., column F).

Similar synergistic effects on the reduction of blood glucose levels were also observed for the combined treatment of metformin and (R)-(+)-verapamil HCl at higher doses, in which the reductions were respectively about 1.11, 1.49 and 1.52 folds (column I, Table 2) over those of control (column F, Table 2) for R-VPM at 30 mg/Kg, bid, and about 1.17, 1.24, and 1.30 folds (column I, Tables 3) over those of control (column F, Table 3) for R-VPM at 50 mg/Kg, bid.

TABLE 1

Synergistic effect of (R)-(+)-verapamil HCl (15 mg/Kg, bid) and metformin on the reduction of blood glucose level in NIDDM mice

| | treatment | | | | | | | | |
|---|---|---|---|---|---|---|---|---|---|
| | Vehicle | metformin | | R-VMP (15 mg/Kg, bid) | | | Combined treatment (R-VMP + Metformin) | | Folds of Reduction |
| day | A | B | C = B − A | D | E = D − A | F = C + E | G | H = G − A | I = H/F |
| 0 | 100 | 100 | 0 | 100 | 0 | 0 | 100 | 0 | — |
| 15 | 97.1 | 65.3 | −31.8 | 99.4 | 2.3 | −29.5 | 54.6 | −42.5 | 1.44 |
| 29 | 116.4 | 103.6 | −12.8 | 121.6 | 5.2 | −7.6 | 81.4 | −35 | 4.61 |
| 43 | 121.6 | 108.8 | −12.8 | 115 | −6.6 | −19.4 | 74 | −47.6 | 2.45 |

TABLE 2

Synergistic effect of (R)-(+)-verapamil HCl (30 mg/Kg, bid) and metformin on the reduction of blood glucose level in NIDDM mice

| | treatment | | | | | | | | |
|---|---|---|---|---|---|---|---|---|---|
| | Vehicle | metformin | | R-VMP (30 mg/Kg, bid) | | | Combined treatment (R-VMP + Metformin) | | Folds of Reduction |
| day | A | B | C = B − A | D | E = D − A | F = C + E | G | H = G − A | I = H/F |
| 0 | 100 | 100 | 0 | 100 | 0 | 0 | 100 | 0 | — |
| 15 | 97.1 | 65.3 | −31.8 | 87.7 | −9.4 | −41.2 | 51.5 | −45.6 | 1.11 |
| 29 | 116.4 | 103.6 | −12.8 | 103.5 | −12.9 | −25.7 | 78.2 | −38.2 | 1.49 |
| 43 | 121.6 | 108.8 | −12.8 | 99.7 | −21.9 | −34.7 | 69 | −52.6 | 1.52 |

TABLE 3

Synergistic effect of (R)-(+)-verapamil HCl (50 mg/Kg, bid) and metformin on the reduction of blood glucose level in NIDDM mice

| | treatment | | | | | | | | |
|---|---|---|---|---|---|---|---|---|---|
| | Vehicle | metformin | | R-VMP (50 mg/Kg, bid) | | | Combined treatment (R-VMP + Metformin) | | Folds of Reduction |
| day | A | B | C = B − A | D | E = D − A | F = C + E | G | H = G − A | I = H/F |
| 0 | 100 | 100 | 0 | 100 | 0 | 0 | 100 | 0 | — |
| 15 | 97.1 | 65.3 | −31.8 | 82.3 | −14.8 | −46.6 | 42.5 | −54.6 | 1.17 |
| 29 | 116.4 | 103.6 | −12.8 | 94.4 | −22 | −34.8 | 73.4 | −43 | 1.24 |
| 43 | 121.6 | 108.8 | −12.8 | 98.7 | −22.9 | −35.7 | 75.2 | −46.4 | 1.30 |

2.2 Glycated Haemolglobin (HbA1c) Level

Another common indicator, glycated haemolglobin (HbA1c), which reflects average blood glucose levels over a duration was also measured in the present study. HbA1c develops when haemolglobin, a protein within red blood cells that carries oxygen throughout the body joins with glucose in the blood and becomes "glycated." Since red blood cells in a human body survive for about 8-12 weeks before renewal, thus, the level of HbA1c gives an overall picture of average blood sugar levels over such period.

Figure 4:
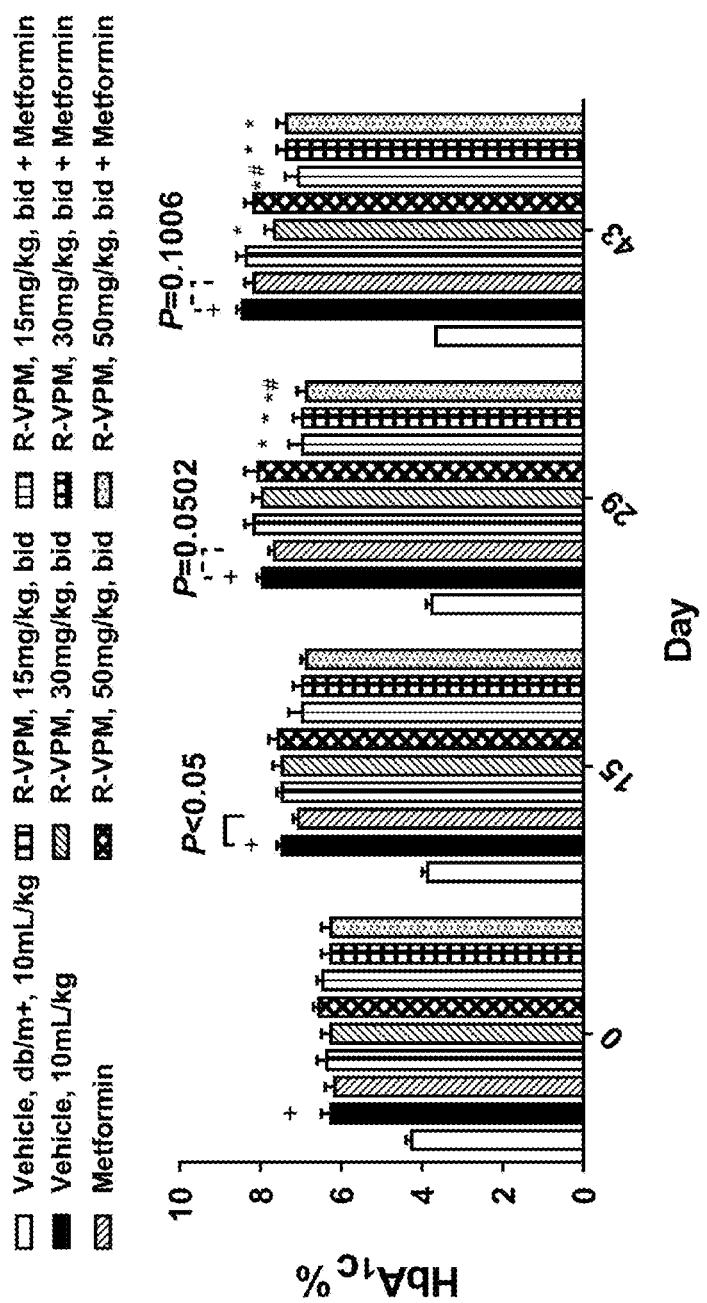
FIG. 4 is a bar graph illustrating the effects of (R)-(+)-verapamil HCl and/or metformin on the level of glycated haemoglobin (HbA1c) in NIDDM mice in accordance with Example 2.2 of this invention, in which differences are considered significant at †$P<0.05$, vs vehicle control (db/m+), *$P<0.05$, vs vehicle control (db/db), #$P<0.05$, vs metformin (db/db). Comparisons of "metformin" and "vehicle control (db/db" is performed using Student's unpaired t-test: significance denoted by solid lines and trends denoted by dashed lines.

Referring to FIG. 4, which depicts the effects of metformin, (R)-(+)-verapamil HCl (R-VPM) or both on the level of HbA1c in NIDDM mice. It was found that metformin significantly reduce HbA1c level, and R-VPM had no effect at the doses of 15 mg/Kg, bid, and mild reduction was observed at the dose of 30 mg/Kg, bid. However, combined treatment with metformin and R-VPM produced a synergistic reduction in the level of HbA1c in NIDDM mice, similar to the findings in Example 2.1. As summarized in Table 4, combined treatment of 15 mg/Kg, bid (R)-(+)-verapamil and metformin resulted in 1.56, 11.94, and 3.84 folds (column I, Table 4) reduction in HbA1c levels were found on days 15, 29, and 43, respectively, as compared to the summation of HbA1c changes resulted from metformin alone and R-VMP alone (column F, Table 4). Similar findings were found in Tables 5 and 6, in which the reduction were respectively about 1.45, 6.71, and 1.13 folds (column I, Table 5) over those of control (column F, Table 5) for R-VMP at 30 mg/Kg, bid, and about 1.10, 2.92 and 1.41 folds (column I, Table 6) over those of control (column F, Table 6) for V-RMP at 50 mg/Kg, bid.

TABLE 4

Synergistic effect of (R)-(+)-verapamil (15 mg/Kg, bid) and metformin on the reduction of HbA1c level in NIDDM mice

| | treatment | | | | | | | | |
|---|---|---|---|---|---|---|---|---|---|
| | Vehicle | metformin | | R-VMP (15 mg/Kg, bid) | | | Combined treatment (R-VMP + Metformin) | | Folds of Reduction |
| day | A | B | C = B − A | D | E = D − A | F = C + E | G | H = G − A | I = H/F |
| 0 | 100 | 100 | 0 | 100 | 0 | 0 | 100 | 0 | — |
| 15 | 120.2 | 114.7 | −5.5 | 117.7 | −2.5 | −8 | 107.7 | −12.5 | 1.56 |
| 29 | 127.4 | 124.9 | −2.5 | 128.3 | 0.9 | −1.6 | 108.3 | −19.1 | 11.94 |
| 43 | 136 | 133 | −3 | 132.2 | −3.8 | −6.8 | 109.9 | −26.1 | 3.84 |

TABLE 5

Synergistic effect of (R)-(+)-verapamil (30 mg/Kg, bid) and metformin on the reduction of HbA1c level in NIDDM mice

| | treatment | | | | | | | | |
|---|---|---|---|---|---|---|---|---|---|
| | Vehicle | metformin | | R-VMP (30 mg/Kg, bid) | | | Combined treatment (R-VMP + Metformin) | | Folds of Reduction |
| day | A | B | C = B − A | D | E = D − A | F = C + E | G | H = G − A | I = H/F |
| 0 | 100 | 100 | 0 | 100 | 0 | 0 | 100 | 0 | — |
| 15 | 120.2 | 114.7 | −5.5 | 119.2 | −1 | −6.5 | 110.8 | −9.4 | 1.45 |
| 29 | 127.4 | 124.9 | −2.5 | 127.5 | 0.1 | −2.4 | 111.3 | −16.1 | 6.71 |
| 43 | 136 | 133 | −3 | 123.2 | −12.8 | −15.8 | 118.1 | −17.9 | 1.13 |

TABLE 6

Synergistic effect of (R)-(+)-verapamil (50 mg/Kg, bid) and metformin on the reduction of HbA1c level in NIDDM mice

| | treatment | | | | | | | | |
|---|---|---|---|---|---|---|---|---|---|
| | Vehicle | metformin | | R-VMP (50 mg/Kg, bid) | | | Combined treatment (R-VMP + Metformin) | | Folds of Reduction |
| day | A | B | C = B − A | D | E = D − A | F = C + E | G | H = G − A | I = H/F |
| 0 | 100 | 100 | 0 | 100 | 0 | 0 | 100 | 0 | — |
| 15 | 120.2 | 114.7 | −5.5 | 115.7 | −4.5 | −10 | 109.2 | −11 | 1.10 |
| 29 | 127.4 | 124.9 | −2.5 | 123.7 | −3.7 | −6.2 | 109.3 | −18.1 | 2.92 |
| 43 | 136 | 133 | −3 | 125.5 | −10.5 | −13.5 | 117 | −19 | 1.41 |

Taken together of the findings in the working examples, (R)-(+)-verapamil HCl alone (≥25 mg/Kg, bid) is effective in reducing blood glucose level, thus is useful for treating diabetes. Most surprisingly is that the combined treatment of metformin (300 mg/Kg) and (R)-(+)-verapamil (≥15 mg/Kg, bid) produces synergistic reduction in blood glucose level, as well as in the level of long-term diabetic indicator—HbA1c. Accordingly, (R)-(+)-verapamil is suitable for use as a lead compound for the development of a blood glucose reduction agent for treating diabetes mellitus and/or disorders related thereto.

It will be understood that the above description of embodiments is given by way of example only and that various modifications may be made by those with ordinary skill in the art. The above specification, examples, and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A method of treating a subject having diabetes mellitus and/or disorders related to diabetes mellitus comprising administering to the subject an effective amount of (R)-(+)-verapamil or a pharmaceutically acceptable salt thereof and biguanide so as to reduce the blood glucose level of the subject.

2. The method of claim 1, wherein the biguanide is metformin, phenformin, or bufomin.

3. The method of claim 1, wherein the (R)-(+)-verapamil or a pharmaceutically acceptable salt thereof is in crystalline form.

4. The method of claim 3, wherein the (R)-(+)-verapamil exists in a hydrochloride salt.

5. The method of claim 4, wherein the (R)-(+)-verapamil hydrochloride is administered to the subject in the amount of 15 to 1,000 mg/day.

6. The method of claim 5, wherein the (R)-(+)-verapamil hydrochloride is administered to the subject in the amount of 25 to 800 mg/day.

* * * * *